(12) United States Patent
Litman et al.

(10) Patent No.: US 9,632,044 B1
(45) Date of Patent: Apr. 25, 2017

(54) IMAGING BOTTOM OF HIGH ASPECT RATIO HOLES

(71) Applicant: APPLIED MATERIALS ISRAEL LTD., Rehovot (IL)

(72) Inventors: Alon Litman, Nes-Ziona (IL); Konstantin Chirko, Rehovot (IL)

(73) Assignee: APPLIED MATERIALS ISREAL LTD., Rehovot (IL)

( * ) Notice: Subject to any disclaimer, the term of this patent is extended or adjusted under 35 U.S.C. 154(b) by 0 days.

(21) Appl. No.: 15/059,063

(22) Filed: Mar. 2, 2016

(51) Int. Cl.
*G01N 23/225* (2006.01)
*H01L 21/67* (2006.01)
*H01L 21/66* (2006.01)

(52) U.S. Cl.
CPC ... *G01N 23/2251* (2013.01); *H01L 21/67253* (2013.01); *H01L 22/12* (2013.01); *G01N 2223/6116* (2013.01)

(58) Field of Classification Search
USPC ........................................ 250/306, 307, 310
See application file for complete search history.

(56) References Cited

U.S. PATENT DOCUMENTS 5,530,372 A * 6/1996 Lee .................... G01R 31/2886
324/754.03

\* cited by examiner

*Primary Examiner* — Kiet T Nguyen
(74) *Attorney, Agent, or Firm* — Kilpatrick Townsend & Stockton LLP

(57) ABSTRACT

A method that includes performing multiple test iterations to provide multiple test results; and processing the multiple test results to provide estimates of a conductivity of each of the multiple bottoms segments. The multiple test iterations includes repeating, for each bottom segment of the multiple bottom segments, the steps of: (a) illuminating the bottom segment by a charging electron beam; wherein electrons emitted from the bottom segment due to the illuminating are prevented from exiting the hole; (b) irradiating, by a probing electron beam, an area of an upper surface of the dielectric medium; (c) collecting electrons emitted from the area of the upper surface as a result of the irradiation of the area by the probing electron beam to provide collected electrons; and (d) determining an energy of at least one of the collected electrons to provide a test result.

13 Claims, 8 Drawing Sheets

IMAGING BOTTOM OF HIGH ASPECT RATIO HOLES

BACKGROUND OF THE INVENTION

Substrates such as wafers are manufactured by highly complicated manufacturing processes. These manufacturing processes should be monitored in order to ensure the quality of the wafers.

Some substrates include holes of high aspect ratio. An aspect ratio is the ratio between a depth of a hole and a width of hole.

A high aspect ratio hole can be defined as a hole that has an aspect ratio that is high enough so that when illuminating the bottom of the hole the electrons that are emitted from the bottom of the hole do not exit the hole.

When illuminating the bottom of a high aspect ratio hole the bottom seems dark—regardless of the composition of the bottom of the hole.

BRIEF SUMMARY OF THE INVENTION

According to an embodiment of the invention there may be provided a method for evaluating multiple bottom segments of a bottom of a hole formed in a dielectric medium. The method can include performing multiple test iterations to provide multiple test results, and processing the multiple test results to provide estimates of a conductivity of each of the multiple bottoms segments. The performing of the multiple test iterations can include repeating, for each bottom segment of the multiple bottom segments, the steps of: (a) illuminating the bottom segment by a charging electron beam, where electrons emitted from the bottom segment due to the illuminating of the bottom segment are prevented from exiting the hole; (b) irradiating, by a probing electron beam, an area of an upper surface of the dielectric medium, where the area belongs to a region of the upper surface that surrounds the hole; (c) collecting electrons emitted from the area of the upper surface as a result of the irradiation of the area by the probing electron beam to provide collected electrons; and (d) determining an energy of at least one of the collected electrons to provide a test result.

According to an embodiment of the invention there may be provided an inspection system that can include an image acquisition unit configured to perform multiple test iterations for testing multiple bottom segments and to provide multiple test results. The inspection system can also include a processor configured to process the multiple test results to provide estimates of a conductivity of each bottom segment of the multiple bottom segments. The image acquisition unit can be configured to perform the multiple test iterations by repeating, for each bottom segment of the multiple bottom segments of a bottom of a hole, the steps of: (a) illuminating the bottom segment by a charging electron beam, where electrons emitted from the bottom segment due to the illuminating of the bottom segment are prevented from exiting the hole; (b) irradiating, by a probing electron beam, an area of an upper surface of a dielectric medium, where the area belongs to a region of the upper surface that surrounds the hole; (c) collecting electrons emitted from the area of the upper surface as a result of the irradiation of the area by the probing electron beam to provide collected electrons; and (d) determining an energy of at least one of the collected electrons to provide a test result.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
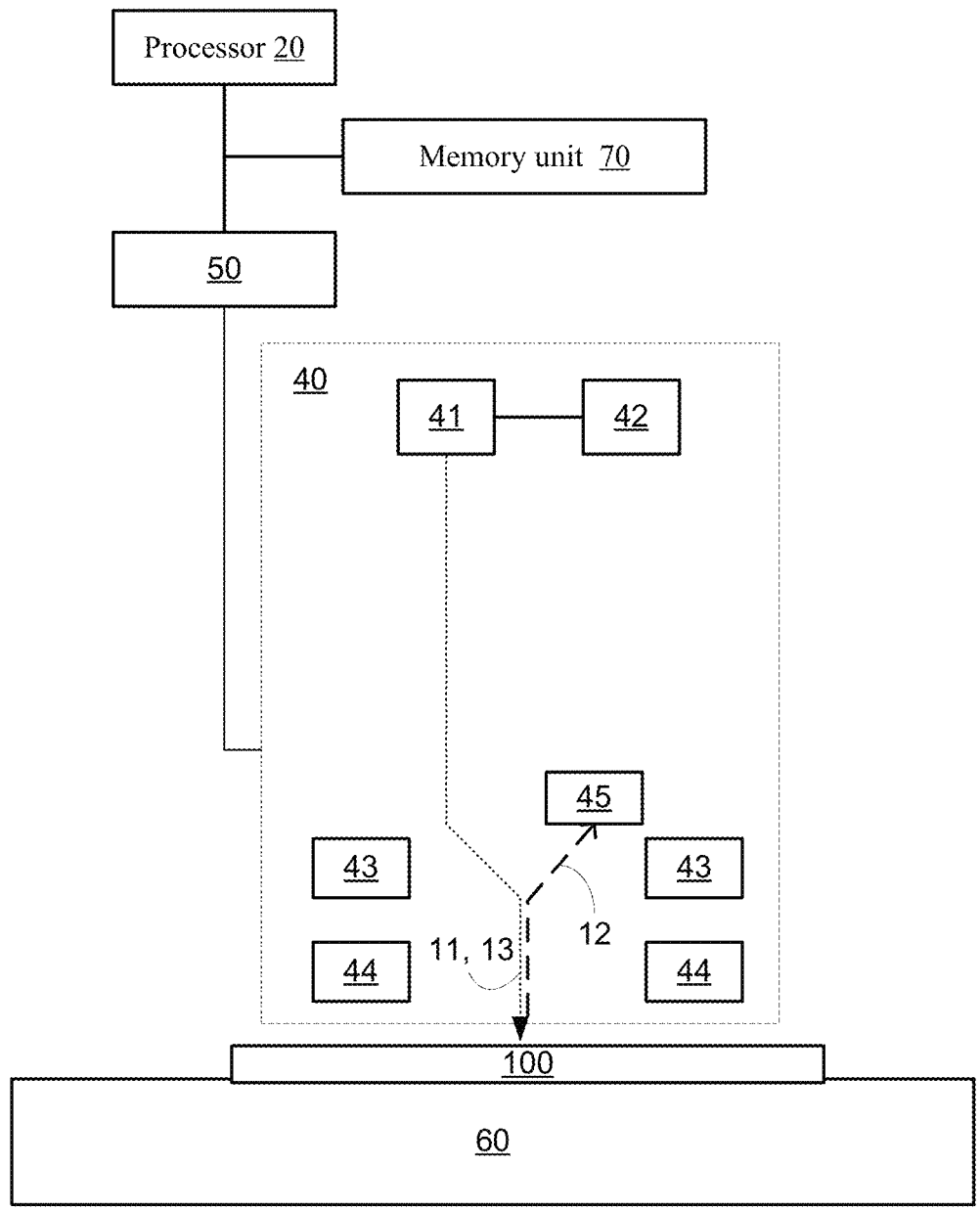
FIG. 1 illustrates a system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

FIG. 1 illustrates inspection system 10 and a substrate 100 according to an embodiment of the invention. Inspection system 10 can include a processor 20, a memory unit 70, a controller 50, an image acquisition module 40 and a mechanical stage 60.

Mechanical stage 60 is configured to move the substrate 100 in relation to the image acquisition module 40. The image acquisition module 40 includes an electron source 41, a supply unit 42 for feeding the electron source 41, one or more electron optic components such as lenses 43 and 44 and a detector 45. The detector 45 can include an electron to photon converter that is followed by a light sensor. Additionally or alternatively, the detector 45 can include an electron sensing component such as an avalanche diode and/or a PIN diode that can directly sense electrons without an electron to photon converter.

The detector 45 can also include an energy analyzer for determining the energy of electrons that are detected by the detector. Alternatively, the detector 45 and the analyzer can be different units that may be spaced apart from each other. Lenses 43 and 44 can be deflecting and/or focusing lenses, objective lenses or any other type of lenses. Lenses 43 and 44 can be magnetic lenses, electrostatic lenses or a combination of both electrical and magnetic lenses.

FIG. 1 illustrates a primary beam that is deflected twice before impinging on substrate 100. It is noted that the number of deflections can differ from two and that the amount and type of electron optical components may differ from those illustrated in FIG. 1. For example, the primary beam may be deflected four times, more than four times or less than four times.

In FIG. 1 electrons emitted from the substrate are deflected toward detector 45. As will be explained below, the electrons are emitted from an upper surface of a dielectric material. The electrons are not emitted from a bottom of a hole formed in the dielectric material. It is noted that image acquisition module 40 can include a beam splitter (not shown) in addition to or instead lenses 43 and 44.

In some embodiments the image acquisition module 40 can include more than a single detector.

Substrate 100 can have an upper layer that is made of a dielectric material. One or more holes can be formed in the dielectric material. In some cases it is impossible to directly image the bottom of the one or more holes since electrons emitted from the bottom of a hole do not exit the hole and thus do not reach detector 45. Nevertheless, electrons that are emitted from the bottom of the hole may charge (for at least a short period) the dielectric material.

After charging the bottom segment the upper surface of the dielectric material is inspected by directing a probing electron beam towards the upper surface. Electrons emitted from the upper surface are detected by the inspection system. The energy of the electrons emitted from the upper surface depends upon the charging of the dielectric material.

The inspection system 10 is configured to monitor the charging of the dielectric material by electrons emitted from different bottom segments of a bottom of a hole by executing multiple test iterations. Each test iteration may be allocated per each bottom segment. It is noted that more than single test iteration may be allocated to the same bottom segment.

By comparing between the energy of electrons that are detected during different (for example—successive) test iterations the inspection system may evaluate which test iterations caused the dielectric material to be charged. For example, assuming that (a) a given bottom segment was charged during an n'th test iteration (n being a positive integer), and (b) that the energy of electrons that were measured in the (n−1)'th test iteration is the same as the energy of electrons that were measured during the n'th test iteration. Under assumptions (a) and (b) it can be concluded that given bottom segment is made of a conductive material.

Yet for another example, assuming that (c) a given bottom segment was charged during an n'th test iteration (n being a positive integer), and (d) that the energy of electrons that were measured in the (n−1)'th test iteration differs from the energy of electrons that were measured during the n'th test iteration. Under assumptions (c) and (d) it can be concluded that given bottom segment is made of a non-conductive material.

The duration of each test iteration may be in the nano-second range (for example—between 1 and 80 nanoseconds), in the sub-nanosecond range or above the nanosecond range.

According to an embodiment of the invention the bottom of the hole is virtually segmented to multiple bottom segments in order to provide a multiple-pixel image of the bottom of the hole. The shape and size of the bottom segments correspond by the shape and size of a charging electron beam than impinges on the bottom of the hole.

Figure 2:
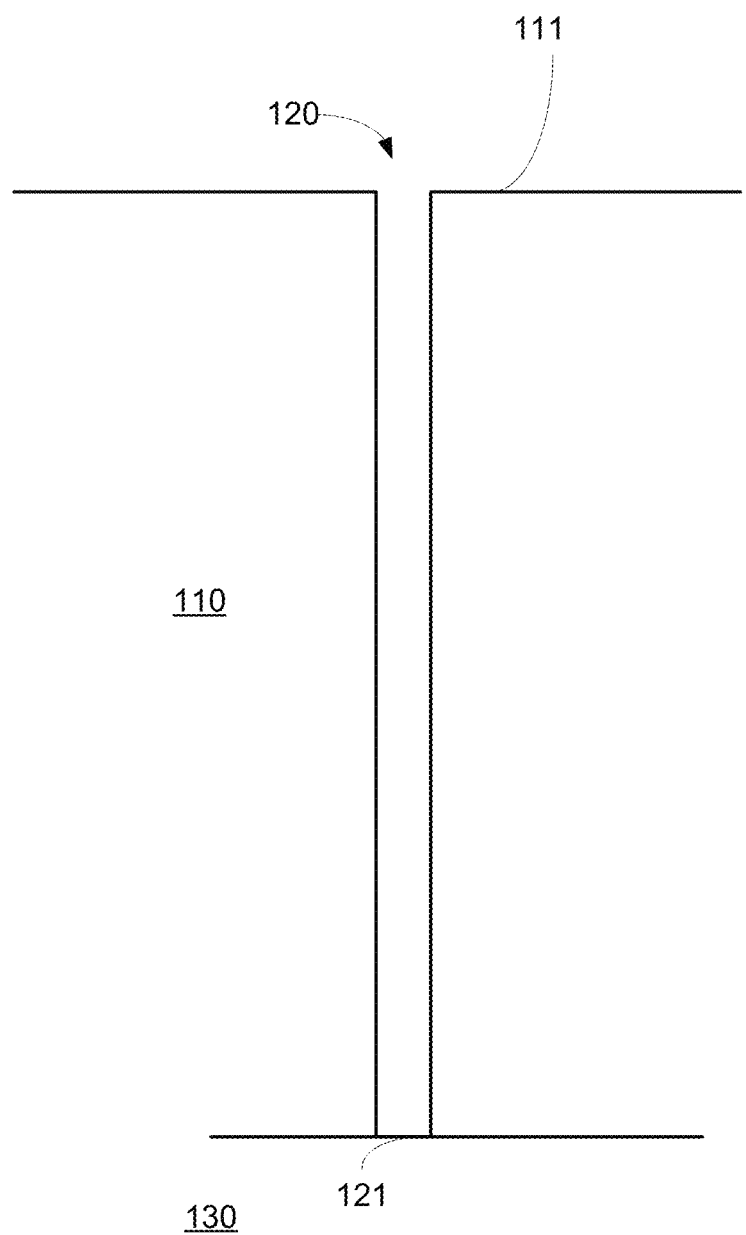
FIG. 2 illustrates a hole and its vicinity.

FIG. 2 is a cross sectional view of a hole 120 and its surroundings. Hole 120 is formed in a dielectric material 110. The dielectric material 110 has an upper surface 111 that surrounds the hole. In FIG. 2 the hole is deep enough to penetrate through the entire dielectric material 110 and expose, at the bottom 121 of the hole 120, another layer 130. It is noted that the other layer may be conductive layer or a non-conductive layer and that foreign particles or residual material may be positioned at the bottom 121 of the hole 120.

Non-limiting examples of the dimensions of the hole are listed below:
 a. Diameter may range between 10 nanometer and 1 micron, (b) Depth may range between 100 nanometers and 10 microns.
 b. Aspect ratio of the hole (diameter divided by depth) may range between 1:3 and 1:100.
 c. The dielectric material can be made of materials such as but not limited to $SiO_2$ and $Si_3N_4$.

Substrate 100 can be made of materials such as but not limited to tungsten (W) and polysilicon.

A typical dies has a size that is smaller than one square centimeter and may include more than a thousand holes.

The image acquisition module 40 is configured to perform multiple test iterations to provide multiple test results by repeating, for each bottom segment of the multiple bottom segments, the steps of:
 (a) Illuminating the bottom segment by a charging electron beam 11. It is noted that electrons emitted from the bottom segment due to the illuminating are prevented from exiting the hole. The emitted electrons charge the dielectric material when the bottom segment is not conductive. No electrons are emitted when the bottom segment is conductive.

(b) Irradiating, by a probing electron beam 13, an area of the upper surface of the dielectric medium; wherein the area belongs to a region of the upper surface that surrounds the hole;

(c) Collecting electrons 12 emitted from the area of the upper surface as a result of the irradiation of the area by the probing electron beam to provide collected electrons.

(d) Determining the energy of at least one of the collected electrons to provide a test result.

FIGS. 3-7 illustrate sixteen bottom segments denoted 1211, 1212, 1213, 1214, 1215, 1216, 1217, 1218, 1221, 1222, 1223, 1224, 1225, 1226, 1227 and 1228 of a bottom 121 of a hole and a region 123 of the upper surface of the dielectric material. Region 123 surrounds the hole.

The number of bottom segments may differ from sixteen. The shape of the bottom segments may differ from those illustrated in FIGS. 3-7.

Figure 3:
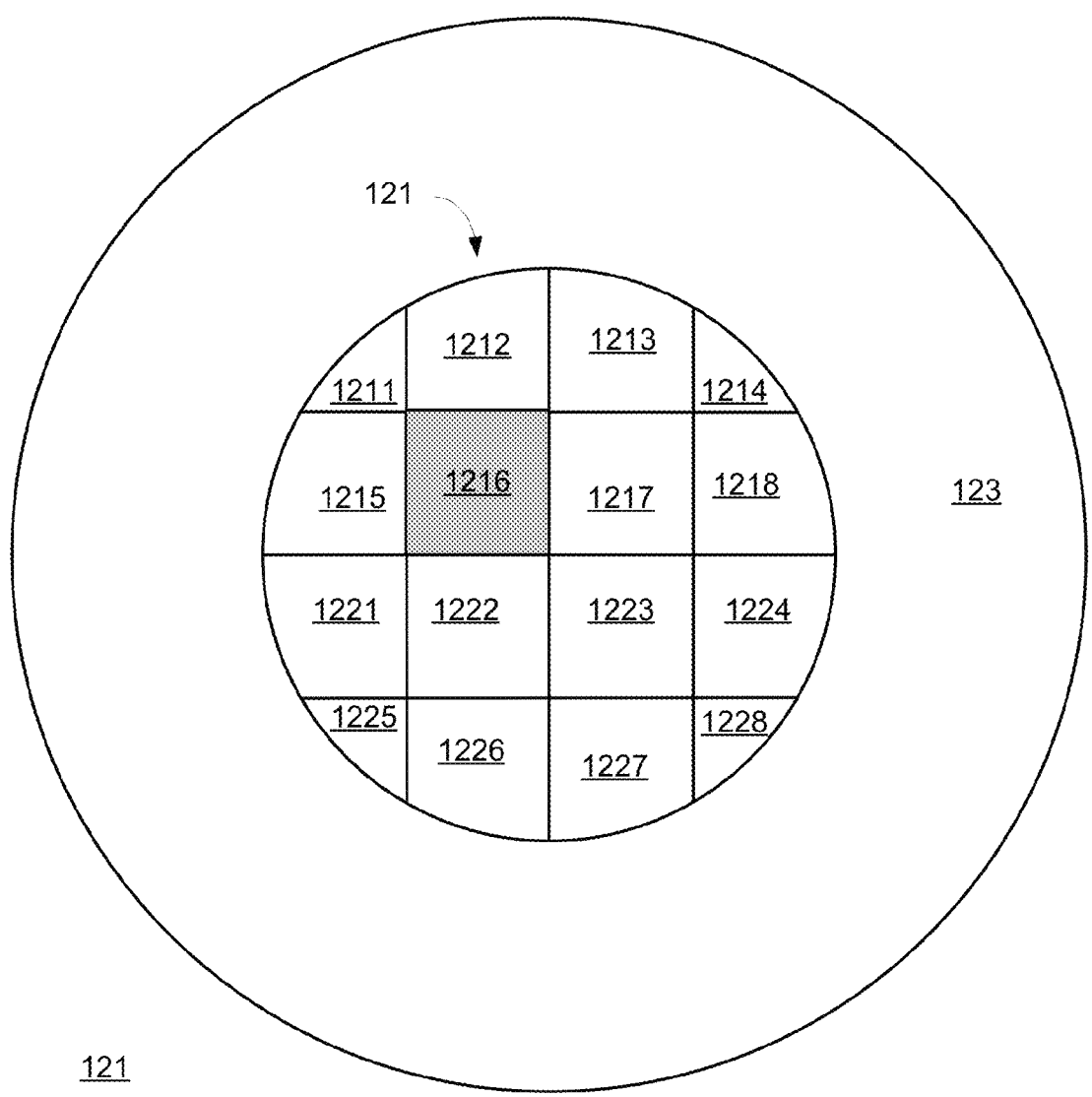
FIG. 3 illustrates an illumination of a bottom segment of a bottom of a hole by a charging electron beam according to an embodiment of the invention.

FIG. 3 illustrates a bottom segment 1216 that is illuminated by a charging electron beam 11 during certain test iteration.

Figure 4:
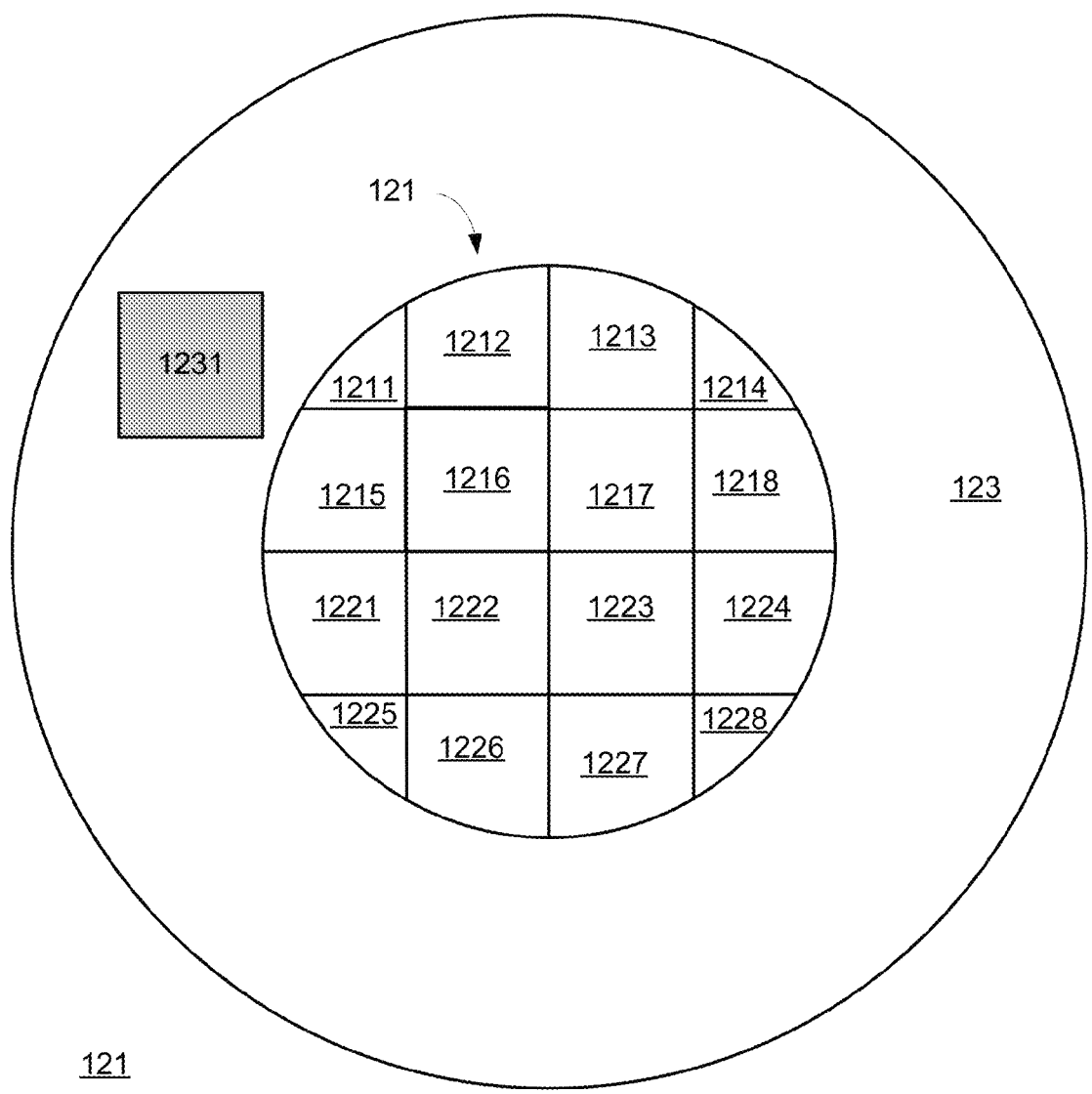
FIG. 4 illustrates an illumination of an area of an upper surface by a probing electron beam according to an embodiment of the invention.

FIG. 4 illustrates area 1231 of the region 123 that is illuminated according to an embodiment of the invention. Area 1231 may be illuminated immediately after the illumination of bottom segment 1216 by a probing electron beam 13. Electrons emitted from area 1231 may be collected by detector 45. The shape and size of area 1231 equal the shape and size of bottom segment 1216.

Figure 5:
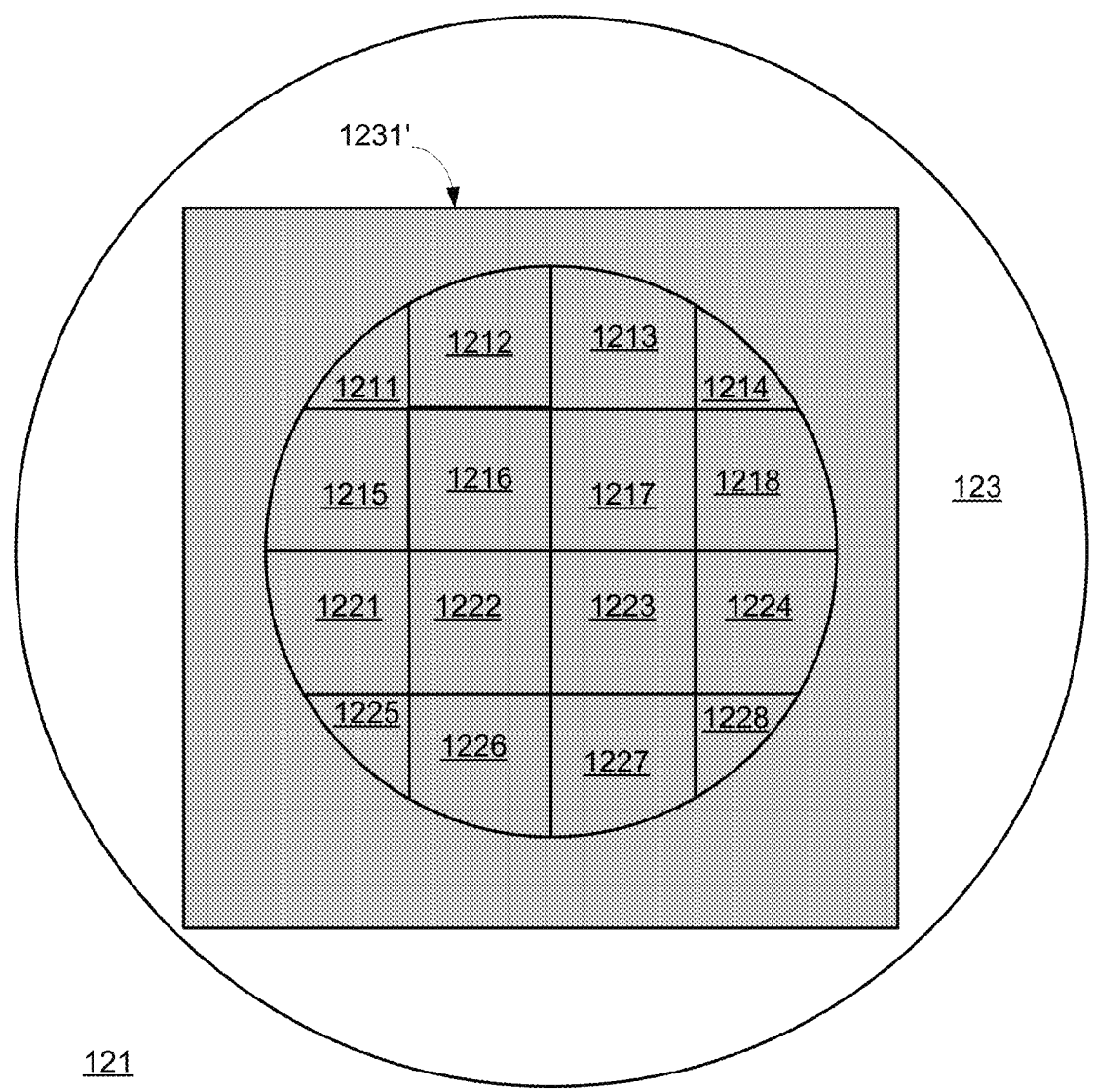
FIG. 5 illustrates an illumination of an area of an upper surface and of the entire bottom of the hole by a probing electron beam according to an embodiment of the invention.

FIG. 5 illustrates an area 1231' that is illuminated according to another embodiment of the invention. Area 1231' includes the entire bottom 121 as well as a part of region 123 that may be illuminated (immediately after the illumination of bottom segment 1216) by probing electron beam 13. Electrons emitted from area 1231' may be collected by detector 45.

Figure 6:
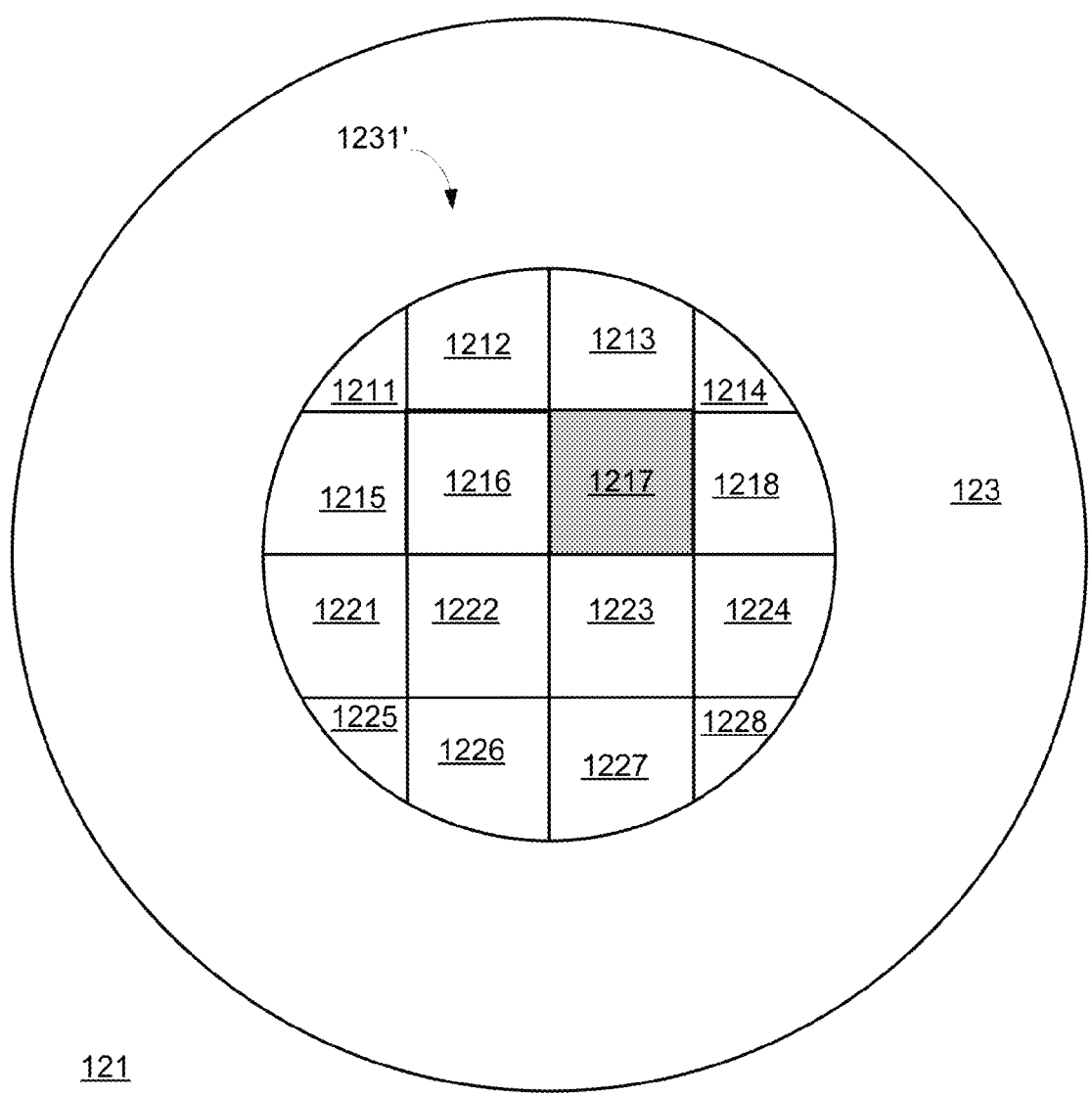
FIG. 6 illustrates an illumination of a bottom segment of a bottom of a hole by a charging electron beam according to an embodiment of the invention.

FIG. 6 illustrates another bottom segment 1217 that is illuminated by a charging electron beam 11 during certain test iterations.

Figure 7:
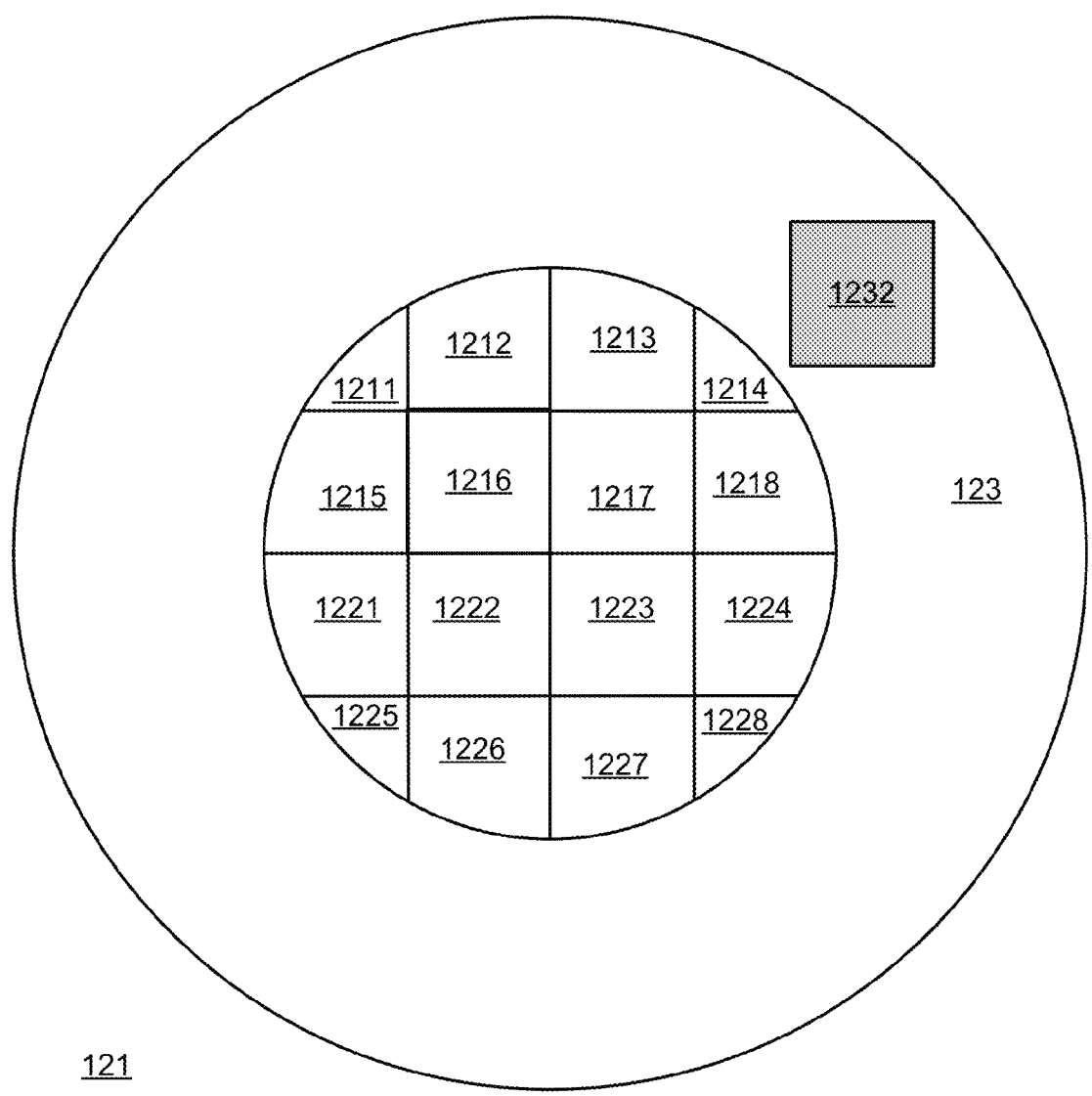
FIG. 7 illustrates an illumination of an area of an upper surface by a probing electron beam according to an embodiment of the invention.

FIG. 7 illustrates area 1232 of the region 123 that is illuminated according to an embodiment of the invention. Area 1232 may be illuminated immediately after the illumination of bottom segment 1217 by a probing electron beam 13. Electrons emitted from area 1232 may be collected by detector 45. The shape and size of area 1232 may equal the shape and size of bottom segment 1216.

It is noted that the inspection system may illuminate area 1231 (FIG. 4) or area 1231' (FIG. 5) immediately after illuminating bottom segment 1217.

The inspection system 10 may compare between signals sensed by detector 45 (test results) obtained during different test iteration in order to evaluate the conductivity of each one of the bottom segments and generate an image of the bottom of the hole that reflects the test results.

FIGS. 3 and 5 illustrate a charging electron beam 11 that is smaller than the probing electron beam 13. These size changes may be generated by (i) changing the supply voltage provided by the supply unit 42 to the electron source, and/or by (ii) changing the focusing parameters of any one of lenses 43 and 44.

FIGS. 3, 4, 6 and 7 illustrate changes in the locations of the charging electron beam 11 versus the probing electron beam 13. These changes may be generated by chancing deflection parameters by any one of lenses 43 and 44.

Figure 8:
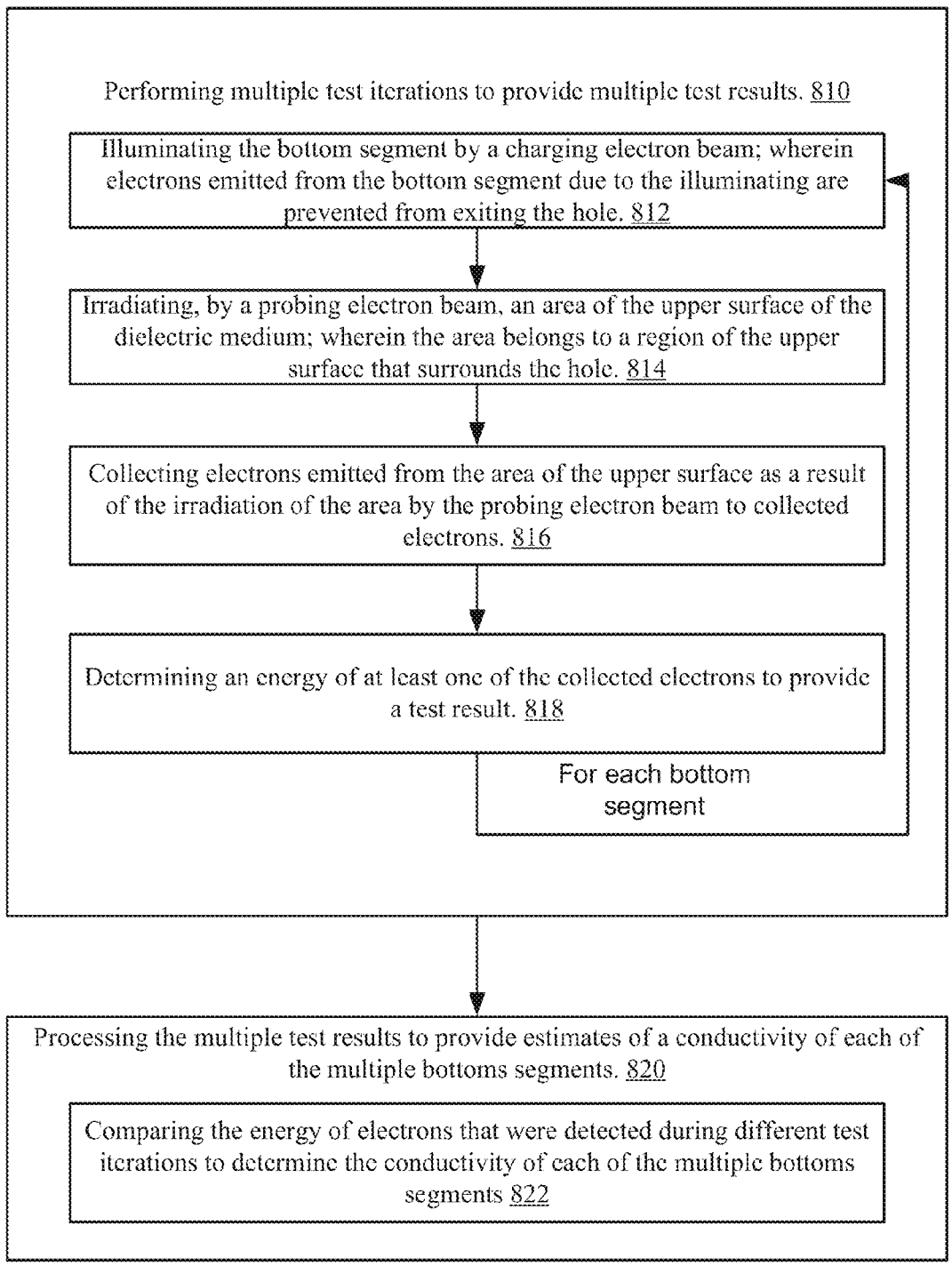
FIG. 8 illustrates a method according to an embodiment of the invention.

FIG. 8 illustrates method 800 according to an embodiment of the invention. Method 800 can start with step 810 by performing multiple test iterations to provide multiple test results. Step 810 can be followed by step 820 of processing the multiple test results to provide estimates of a conductivity of each of the multiple bottoms segments.

Step 810 can include repeating, for each bottom segment of the multiple bottom segments, the steps of:

a. Step 812 of illuminating the bottom segment by a charging electron beam; wherein electrons emitted from the bottom segment due to the illuminating are prevented from exiting the hole.

b. Step 814 of irradiating, by a probing electron beam, an area of the upper surface of the dielectric medium; wherein the area belongs to a region of the upper surface that surrounds the hole.

c. Step 816 of collecting electrons emitted from the area of the upper surface as a result of the irradiation of the area by the probing electron beam to provide collected electrons.

d. Step 818 of determining an energy of at least one of the collected electrons to provide a test result.

Step 820 can include step 822 of comparing the energy of electrons that were detected during different test iterations to determine the conductivity of each of the multiple bottoms segments.

Step 822 can include determining the conductivity of each bottom segment based on a difference between successive test iterations. A bottom segment may be deemed conductive when the test iteration that tested the bottom segment did not change the energy of the electrons emitted from the upper surface.

The invention can also be implemented in a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups.

A computer program is a list of instructions such as a particular application program and/or an operating system. The computer program can, for instance, include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program can be stored internally on a non-transitory computer readable medium. All or some of the computer program can be provided on computer readable media permanently, removable or remotely coupled to an information processing system. The computer readable media can include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as flash memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system can for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein can be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for evaluating multiple bottom segments of a bottom of a hole formed in a dielectric medium, the method comprising:
  performing multiple test iterations to provide multiple test results; and
  processing the multiple test results to provide estimates of a conductivity of each of the multiple bottoms segments;
  wherein the performing of the multiple test iterations comprises repeating, for each bottom segment of the multiple bottom segments, the steps of:
  (a) illuminating the bottom segment by a charging electron beam; wherein electrons emitted from the bottom segment due to the illuminating of the bottom segment are prevented from exiting the hole;
  (b) irradiating, by a probing electron beam, an area of an upper surface of the dielectric medium; wherein the area belongs to a region of the upper surface that surrounds the hole;
  (c) collecting electrons emitted from the area of the upper surface as a result of the irradiation of the area by the probing electron beam to provide collected electrons; and
  (d) determining an energy of at least one of the collected electrons to provide a test result.

2. The method according to claim 1 wherein the probing electron beam is wider than the charging electron beam.

3. The method according to claim 1 comprising a primary electron beam to provide the probing electron beam and focusing the primary electron beam to provide the charging electron beam.

4. The method according to claim 1 wherein the probing electron beam further illuminates the hole.

5. The method according to claim 1 wherein a size of the probing electron beam equals a size of the charging electron beam.

6. The method according to claim 1 wherein a duration of each test iteration does not exceed one microsecond.

7. An inspection system, comprising:
  an image acquisition unit that is configured to perform multiple test iterations for testing multiple bottom segments and to provide multiple test results; and
  a processor that is configured to process the multiple test results to provide estimates of a conductivity of each bottom segment of the multiple bottom segments;
  wherein the image acquisition unit is configured to perform the multiple test iterations by repeating, for each bottom segment of the multiple bottom segments of a bottom of a hole, the steps of:
  (a) illuminating the bottom segment by a charging electron beam; wherein electrons emitted from the bottom segment due to the illuminating of the bottom segment are prevented from exiting the hole;
  (b) irradiating, by a probing electron beam, an area of an upper surface of a dielectric medium; wherein the area belongs to a region of the upper surface that surrounds the hole;
  (c) collecting electrons emitted from the area of the upper surface as a result of the irradiation of the area by the probing electron beam to provide collected electrons; and
  (d) determining an energy of at least one of the collected electrons to provide a test result.

8. The inspection system according to claim 7 wherein the probing electron beam is wider than the charging electron beam.

9. The inspection system according to claim 7 wherein the image acquisition unit comprises a focusing lens that is configured to defocus a primary electron beam to provide the probing electron beam and focus the primary electron beam to provide the charging electron beam.

10. The inspection system according to claim 7 wherein the image acquisition unit comprises an electron source for outputting electrons and an supply unit that is configured to (a) supply to the electron source a supply voltage of a first value to provide the probing electron beam, and (b) supply to the electron source a supply voltage of a second value to provide the charging electron beam; and wherein the first value differs from the second value.

11. The inspection system according to claim 7 wherein the image acquisition unit is configured to generate the probing electron beam that further illuminates the hole.

12. The inspection system according to claim 7 wherein a size of the probing electron beam equals a size of the charging electron beam.

13. The inspection system according to claim 7 wherein a duration of each test iteration does not exceed one nanoseconds.

* * * * *